United States Patent [19]

Shigekawa

[11] 4,078,417

[45] Mar. 14, 1978

[54] TEST PANEL FOR EVALUATING INSPECTION PENETRANTS

[75] Inventor: Toy T. Shigekawa, Loomis, Calif.

[73] Assignee: The United States of America as represented by the Secretary of the Air Force, Washington, D.C.

[21] Appl. No.: 780,956

[22] Filed: Mar. 24, 1977

[51] Int. Cl.² .................................... G01N 19/08
[52] U.S. Cl. ............................................. 73/1 R
[58] Field of Search .......................... 73/1 R, 104

[56] References Cited

U.S. PATENT DOCUMENTS

| | | | |
|---|---|---|---|
| 3,164,006 | 1/1965 | Alburger | 73/104 X |
| 3,791,198 | 2/1974 | Alburger | 73/104 X |
| 3,927,551 | 12/1975 | Alburger | 73/1 R |
| 3,946,597 | 3/1976 | Tahbaz | 73/104 X |

*Primary Examiner*—S. Clement Swisher
*Attorney, Agent, or Firm*—Joseph E. Rusz; William J. O'Brien

[57] ABSTRACT

A test panel for use in evaluating fluorescent penetrants and being composed of a spring steel substrate having surfaces coated with a thin electroless nickel plating capable of producing stress induced microcracks in the plated surfaces.

2 Claims, No Drawings

TEST PANEL FOR EVALUATING INSPECTION PENETRANTS

STATEMENT OF GOVERNMENT INTEREST

The invention described herein may be manufactured and used by or for the Government for governmental purposes without the payment of any royalty thereon.

BACKGROUND OF THE INVENTION

This invention relates to a method for evaluating the effectiveness of inspection penetrants. In a more particular aspect, this invention relates to a method and testing panel for ascertaining the flaw detection capabilities of fluorescent inspection penetrants.

The inspection of metal products in order to determine their conformance to predetermined standards of quality is of critical importance in the metal fabrication industry. The inspection and detection of flaws generally takes the form of visual testing or the utilization of various test instruments such as x-ray machines necessity for establishing a reliable and economical testing procedures is common to all product manufacturing. It is especially necessary in the fabrication of metal castings and machine parts which are often characterized by surface flaws and defects. Shrinkage cavities, microcracks blowholds and the like are not readily discernable by visual inspection. Consequently, industry has developed a testing method which utilizes various types of penetrating solutions for detecting such flaws. Usually, the penetrant is applied to the surface of the metal part. The solution is then washed or wiped off the surface to remove excess penetrant. Sufficient time is allowed to lapse in order to allow the penetrant to seep to the surface. The penetrant agent can then be detected visually by its color or luminescence.

The penetrant inspection method obviously provides a reliable and economical method of testing. As a result, a considerable research effort has been generated in an attempt to provide penetrants which are even more economical, more efficient and useful for particular or specific testing situations. The evaluation of solutions as candidates for a penetrating inspection procedure often becomes time consuming and expensive. Therefore, a simple and economical means for evaluating penetrant solutions evolved through the use of test panels having surface cracks and defects of known dimension. Various types were fabricated and one of the earliest was the heated aluminum block in which cracks were induced by sudden quenching in ice water.

Another type developed was the chrome-cracked plate in which a sheet of copper is plated with layers of nickel and chromium in specific thicknesses. Since the chrome layer is brittle, cracks are easily induced. Still another type of cracked test panel was constructed by plating a soft metal such as copper with a brittle metal, such as iron. In the utilization of all of these test panels, the cracks are generated in the brittle surface by bending the panel over a curved form or arbor, and then straightened or flattened. The straightening process, however, tends to close up the surface cracks so that their width is on the order of 0.1 micron or less. In order to provide an effective and useful test panel, rigid controls under strict laboratory conditions were required. This resulted in an added expense to the testing procedure. With the present invention, however, it was found that the problems encountered in using rigid controls and stringent laboratory conditions could be avoided by fabricating the panels from spring steel having an electroless coating of nickel. The resulting panel provides an efficient testing device for fluorescent penetrants. It is considerably more sensitive than the previously used cracked aluminum block and can be fabricated on a production basis without the need for expensive laboratory controls and conditions.

SUMMARY OF THE INVENTION

In accordance with this invention, it has been found that cracked plates suitable for use as a testing device in the evaluation of fluorescent penetrants may be fabricated by coating spring tempered high carbon steel with a catalytic nickel alloy plating also known as electroless nickel plating. The thickness of the plating may range from about 0.0005 inch to as much as about 0.0010 inch. The thinly coated, nickel plated steel panel is then bent over a curved form of suitable radius to crack the nickel coating. The plate flattens out as soon as it is removed from the bending jig and the resulting cracks in the nickel plated surface can then be utilized for fluorescent penetrant testing.

Accordingly, the primary object of this invention is to provide a testing device for use in the evaluation testing of fluorescent penetrants.

Another object of this invention is to provide a test panel having survace cracks of a desired dimensional range capable of a high degree of sensitivity to the fluorescent effects of penetrant inspection agents.

Still another object of this invention is to provide a test panel for evaluating the flow detection capabilities of of fluorescent penetrants that is simple in design, amenable to high speed manufacturing techniques, and economical to produce.

The above and still other objects and advantages of the present invention will become more readily apparent upon consideration of the following detailed description thereof.

DESCRIPTION OF THE PREFERRED EMBODIMENT

In accordance with this invention, the objects and advantages referred to hertofore are attained by providing a cracked test panel fabricated from spring tempered high carbon steel coated with an electroless nickel plating approximately 0.0005 to 0.0010 inches in thickness.

Present methods for evaluating fluorescent penetrants most often rely upon the use of quenched, cracked aluminum blocks. These blocks, however, are not sufficiently sensitive to provide a proper evaluation of proposed candidates for use as a fluoroscent penetrating agent. The use of electroplated nickel-chromium crack plates of brass or copper demonstrate sensitivity, but are very expensive to produce since stringent laboratory conditions must be adhered to in order to provide surface cracks of uniform size and configuration. The cracked test panels of this invention, however, overcomes the problems referred to above and provide an economical reliable and efficient means for evaluating fluorescent penetrants.

The cracked plates contemplated by this invention are fabricated in accordance with the following described techniques.

Flat plates or panels of high carbon steel, 3 inches in width, 4 inches in length, and 0.015 inches in depth are heat treated to spring temper using conventional tempering techniques in which the panels are heated to a temperature of 900° F and quenched in oil and drawn at 300° to 400° F. The panels of spring steel are then cleaned and coated with electroless-nickel plating in a conventional shop production electroless nickel plating tank with a deposit of 0.0007 to 0.0010 inches of nickel on both sides. After cooling, the nickel coated panel is bent over a metal arbor of suitable diameter to crack the nickel coating. For example, an arbor of 13 inches diameter can be used to bend the plates and if it does not crack, arbors of successively smaller diameters can be used, such as 12, 11, 10, 9, 8 etc. inches in diameter until cracks of uniform size and configuration are formed. Since the substrate of the panel is spring steel, the plate is not permanently bent and readily returns to a flat condition. The size and number of cracks in a given panel will vary depending on several factors such as plating thickness and the degree of bending.

The test panels are then evaluated by treating them with fluorescent penetrant, removing excess penetrant and applying a conventional developer to bring out the visual indications denoting the presence of cracks, when examined under ultra violet light. An examination of a number of cracked panels will reveal that there is a variation in the number and size of cracks and the panels can then be classified as to the size of the cracks as fine, medium or coarse crack panels. The panels with the very finest cracks are useful with the most sensitive penetrants whereas those with medium or coarse cracks are more suitable for use with medium sensitive penetrants.

Although the invention has been described by reference to particular embodiments, it is to be understood by those skilled in the art that all the various modifications that are encompassed within the scope of the appended claims are intended to be included herein.

What is claimed is:

1. A test panel for use in evaluating the performance capabilities of fluorescent penetrants comprising a spring steel substrate coated with a brittle electroless nickel plating of approximately 0.0005 to 0.0010 inches in depth with stress induced microcracks being present in the plated surfaces of said panel.

2. A test panel in accordance with claim 1 in which said surface is coated with a fluorscent penetrating agent that permeates the stress induced microcracks.

* * * * *